United States Patent
Lee et al.

(10) Patent No.: US 9,241,471 B2
(45) Date of Patent: Jan. 26, 2016

(54) PRAIRIE CORDGRASS (SPARTINA PECTINATA) CULTIVAR 'SAVOY' FOR A BIOENERGY FEEDSTOCK PRODUCTION

(71) Applicant: The Board of Trustees of the University of Illinois, Urbana, IL (US)

(72) Inventors: Dokyoung Lee, Champaign, IL (US); Allen Parrish, Saint Joseph, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 358 days.

(21) Appl. No.: 13/907,181

(22) Filed: May 31, 2013

(65) Prior Publication Data

US 2013/0333067 A1 Dec. 12, 2013

Related U.S. Application Data

(60) Provisional application No. 61/658,376, filed on Jun. 11, 2012.

(51) Int. Cl.
| | | |
|---|---|---|
| *A01H 5/10* | (2006.01) | |
| *A01H 5/12* | (2006.01) | |
| *E02B 3/04* | (2006.01) | |
| *E02D 3/00* | (2006.01) | |
| *B09C 1/00* | (2006.01) | |
| *C10L 5/44* | (2006.01) | |

(52) U.S. Cl.
CPC .. *A01H 5/12* (2013.01); *B09C 1/00* (2013.01); *C10L 5/44* (2013.01); *C10L 5/445* (2013.01); *E02B 3/04* (2013.01); *E02D 3/00* (2013.01); *Y02E 50/10* (2013.01); *Y02E 50/30* (2013.01)

(58) Field of Classification Search
None
See application file for complete search history.

(56) References Cited

PUBLICATIONS

Fu, C. et al. PNAS (Mar. 1, 2011) vol. 108, No. 9, pp. 3803-3808.*

\* cited by examiner

*Primary Examiner* — Russell Kallis
(74) *Attorney, Agent, or Firm* — Morrison & Foerster LLP

(57) ABSTRACT

A new synthetic cultivar of prairie cordgrass designated 'Savoy' is described. 'Savoy' is well adapted to the lower Midwest environment of the United States of America, and has a higher biomass yield potential than presently available commercial prairie cordgrass cultivars, such as 'Red River'. In particular, compared to 'Red River', the cultivar 'Savoy' has higher mass per tiller, more leaves per tiller, higher shoot height and longer, wider leaves containing more biomass per leaf.

19 Claims, 1 Drawing Sheet
(1 of 1 Drawing Sheet(s) Filed in Color)

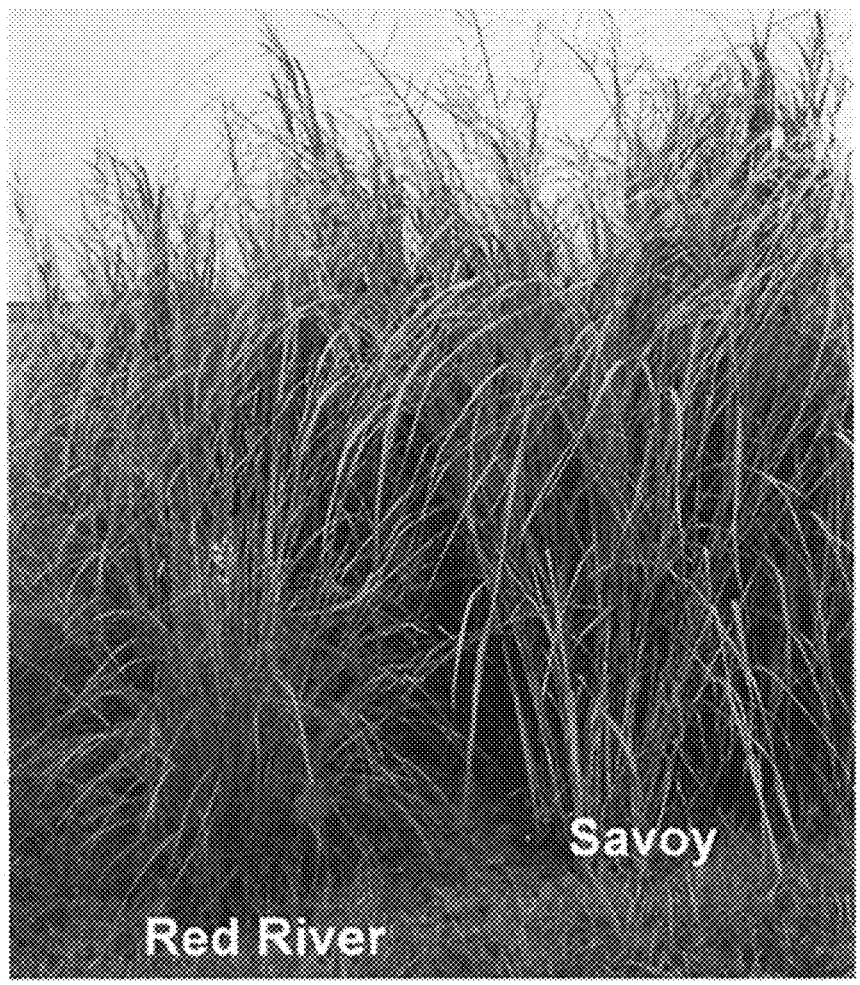

PRAIRIE CORDGRASS (SPARTINA PECTINATA) CULTIVAR 'SAVOY' FOR A BIOENERGY FEEDSTOCK PRODUCTION

RELATED APPLICATION

This application claims the benefit under 35 USC 119(e) of U.S. Provisional Patent Application No. 61/658,376, filed Jun. 11, 2012, the disclosure of which is hereby incorporated by reference in its entirety.

FIELD

The present disclosure relates to a new and distinctive synthetic cultivar of prairie cordgrass (Spartina pectinata) designated 'Savoy'.

BACKGROUND

Prairie cordgrass, Spartina pectinata, is a common species of cordgrass found in the North American tall grass prairie. This species is well adapted to land that becomes seasonally saturated with water or has high concentrations of salts. These characteristics give this species the ability to grow in areas where other plant species cannot survive.

Recently, prairie cordgrass has been recognized as a dedicated energy crop for sustainable feedstock production on marginal lands and an excellent plant species for riparian revegetation and stream bank stabilization. Currently, only one germplasm, 'Red River', is commercially available for seed production and use. However, this germplasm is not well adapted to the lower Midwest, especially south of 43° N, since 'Red River' originated north of 45° N. Outside of this geographic range, the current cordgrass cultivar 'Red River' does not grow optimally, and in particular, does not meet its full biomass yield potential.

Thus, there is a need for novel cultivars of prairie cordgrass capable of growth in a broader geographic region than current commercially available cultivars and that have a higher biomass yield potential than presently available commercial prairie cordgrass cultivars.

BRIEF SUMMARY

In order to meet this need, the present disclosure provides an improved synthetic cultivar of prairie cordgrass designated 'Savoy' having ATCC Accession Number PTA-120691 that is well adapted to the lower Midwest environment of the United States of America, and that has a higher biomass yield potential than presently available commercial prairie cordgrass cultivars, such as 'Red River'.

Accordingly, in certain aspects, the present disclosure provides seed of prairie cordgrass cultivar designated 'Savoy', representative seed of said cultivar having been deposited under ATCC Accession Number PTA-120691. In certain embodiments, the present disclosure provides a prairie cordgrass plant and parts isolated therefrom produced by growing 'Savoy' prairie cordgrass seed. In certain embodiments, the present disclosure provides a prairie cordgrass plant and plant part isolated therefrom having all the physiological and morphological characteristics of a prairie cordgrass plant produced by growing 'Savoy' prairie cordgrass seed having ATCC Accession Number PTA-120691. Prairie cordgrass plant parts include leaves, blades, stalks, shoots, rhizomes, and tillers. Thus, in certain embodiments, the 'Savoy' prairie cordgrass plant part is a leaf, a blade, a stalk, a shoot, a rhizome, a tiller, or a portion thereof. In certain embodiments, the present disclosure provides pollen from a 'Savoy' prairie cordgrass plant, where the 'Savoy' plant is grown from 'Savoy' seed having ATCC Accession Number PTA-120691. In certain embodiments, the present disclosure provides an ovule from a 'Savoy' prairie cordgrass plant, where the 'Savoy' plant is grown from 'Savoy' seed having ATCC Accession Number PTA-120691. In certain embodiments, the present disclosure provides tissue culture from a 'Savoy' prairie cordgrass plant, where the 'Savoy' plant is grown from 'Savoy' seed having ATCC Accession Number PTA-120691.

Other aspects of the present disclosure relate to a method of producing prairie cordgrass seed, by: a) crossing prairie cordgrass cultivar designated 'Savoy' with itself or another prairie cordgrass, where representative seed of the cultivar 'Savoy' has been deposited under ATCC Accession Number PTA-120691; and b) harvesting seed therefrom. In certain embodiments, the present disclosure provides a cordgrass plant or a part thereof, produced by growing the seed produced by the method of the preceding embodiment.

Other aspects of the present disclosure relate to a method of producing a hybrid prairie cordgrass seed, by: a) crossing a first prairie cordgrass plant with a second prairie cordgrass plant, where the first or second prairie cordgrass plant is a 'Savoy' prairie cordgrass plant, where the 'Savoy' plant is grown from 'Savoy' seed having ATCC Accession Number PTA-120691; and b) harvesting seed therefrom. In certain embodiments, the present disclosure provides hybrid prairie cordgrass seed produced by the method of the preceding embodiment. In certain embodiments, the present disclosure provides a hybrid cordgrass plant or a part thereof, produced by growing the hybrid prairie cordgrass seed of the preceding embodiment.

Other aspects of the present disclosure relate to a method of selecting prairie cordgrass, by: a) growing more than one prairie cordgrass plant from prairie cordgrass seed having ATCC Accession Number PTA-120691; and b) selecting one or more plants from step a). In certain embodiments, the present disclosure provides prairie cordgrass plants, plant parts and seeds produced by the prairie cordgrass plants, where the prairie cordgrass plants are isolated by the selection method of the preceding embodiment.

In certain embodiments, the present disclosure provides a bioenergy feedstock produced from a 'Savoy' plant or part thereof, where the 'Savoy' plant is grown from 'Savoy' seed having ATCC Accession Number PTA-120691. In certain embodiments, the present disclosure provides a biofuel produced from the bioenergy feedstock of the preceding embodiment.

Other aspects of the present disclosure relate to a method of producing a bioenergy feedstock, by: a) obtaining biomass derived from a 'Savoy' plant or part thereof, where the 'Savoy' plant is grown from 'Savoy' seed having ATCC Accession Number PTA-120691; and b) processing the biomass to producing a bioenergy feedstock. In certain embodiments, processing the biomass includes pretreating the biomass. In certain embodiments, the pretreating includes chemical pretreatment of the biomass, physical pretreatment of the biomass, biological pretreatment of the biomass, or a combination thereof. In certain embodiments, the method of producing a bioenergy feedstock further includes the step of producing a biofuel from the bioenergy feedstock.

Other aspects of the present disclosure relate to a method of controlling soil erosion, by growing prairie cordgrass plants from prairie cordgrass seed having ATCC Accession Number PTA-120691 under conditions suitable for the resulting plants to control soil erosion.

Other aspects of the present disclosure relate to a method of stabilizing a stream bank, by growing prairie cordgrass plants from prairie cordgrass seed having ATCC Accession Number PTA-120691 under conditions suitable for the resulting plants to control soil erosion along the stream bank, thereby stabilizing the stream bank.

Other aspects of the present disclosure relate to a method for remediating an area in need thereof, by growing prairie cordgrass plants from prairie cordgrass seed having ATCC Accession Number PTA-120691 under conditions suitable for the resulting plants to revegetate the area, thereby remediating the area.

Other aspects of the present disclosure relate to a method for remediating salt-affected soil, by: a) growing prairie cordgrass plants from prairie cordgrass seed having ATCC Accession Number PTA-120691 under conditions sufficient for the resulting plants to absorb salt from the salt-affected soil; and harvesting the plants, thereby removing the salt from the soil.

BRIEF DESCRIPTION OF THE DRAWINGS

The patent or application file contains at least one drawing executed in color. Copies of this patent or application file publication with color drawings will be provided by the office upon request and payment of the necessary fee.

FIG. 1 depicts a picture comparing the 'Savoy' prairie cordgrass (*Spartina pectinata*) with the 'Red River' prairie cordgrass (*Spartina pectinata*).

DETAILED DESCRIPTION

The present disclosure relates to novel synthetic cultivars of prairie cordgrass, such as 'Savoy', and is based, at least, in part, on a selective breeding approach utilizing natural populations of prairie cordgrass. Prairie cordgrass is a very rigid, upright, robust perennial monocot grass, with tough leaves. Rhizomes with the ability to grow 5-10 feet per year distinguish prairie cordgrass from other native warm season grasses. Prairie cordgrass can typically be found throughout the Northeast, Great Lakes and parts of the Midwestern states of the United States of America.

The improved synthetic cultivar 'Savoy' is well adapted to the lower Midwest environment of the United States of America, especially south of 43° N, and has a higher biomass yield potential than presently available commercial prairie cordgrass cultivars, such as 'Red River'. In particular, compared to 'Red River', improved cultivar 'Savoy' has higher mass per tiller, more leaves per tiller, higher shoot height, and longer, wider leaves consisting of more biomass per leaf. Biomass derived from prairie cordgrass, such as improved cultivar 'Savoy', may be used to produce bioenergy feedstocks and biofuel. Improved cultivar 'Savoy' may also be used in stream bank stabilization, bioconservation and/or remediation.

Origin of the Cultivar 'Savoy'

During year 1, seeds collected from 10 natural populations of prairie cordgrass collected throughout Illinois were planted in a greenhouse at Urbana, Ill. Seedlings produced from the greenhouse planting were transplanted to a field at Urbana, Ill. during the spring of year 2. For each population, more than 100 genotypes were transplanted for observation.

Based on variation for biomass yield among the 10 natural populations, 'IL-102' was selected for its high biomass yield potential. In addition, based on other agronomic traits, including plant height, tiller density, and tiller mass, the most desirable 20 genotypes within 'IL-102' were identified. About 25 ramets of each of the best 20 genotypes were established in an isolated crossing block for seed production. The first generation (Syn 1) seed of this 20-genotype synthetic cultivar derived-population was named 'Savoy'.

Accordingly, 'Savoy' is an open pollinated, phenotypically selected synthetic cultivar population that has shown uniformity for its defining trait geographic adaptation, biomass yield, tiller mass yield, and height. Moreover, since the selection was performed based on the phenotypic similarity of 20 individual genotypes within a sample of more than 100 genotypes from the parent population 'IL-102', 'Savoy' is phenotypically uniform for the defining traits even though there is inherent genetic variation within the synthetic cultivar due to the large number (i.e., 20) of genotypes included. Accordingly, unlike true breeding inbred lines, the open pollinated synthetic cultivar 'Savoy' exhibits some degree of variation in quantitative traits, such as yield, height, tiller mass, and density. For example, 'Savoy' exhibits a yield variation of approximately 8.5% (C.V.=8.5%), a height variation of approximately 6.7% (C.V.=6.7%), a tiller mass variation of approximately 12.3% (C.V.=12.3%), and a density variation of approximately 9.7% (C.V.=9.7%).

Prairie Cordgrass Breeding

Prairie cordgrass (*Spartina pectinata*) cultivars of the present disclosure, such as 'Savoy', may be developed for use in the production of hybrid prairie cordgrass cultivars. For example, cultivars may be produced to introduce the traits or characteristics of 'Savoy' into other prairie cordgrass lines. However, cultivars such as 'Savoy' can also provide a source of breeding material that may be used to develop new prairie cordgrass inbred cultivars. Examples of cordgrass species and hybrids include, without limitation, *Spartina alterniflora, Spartina anglica, Spartina baker, Spartina×caespitosa, Spartina cynosuroides, Spartina densiflora, Spartina foliosa, Spartina gracilis, Spartina maritima, Spartina patens, Spartina pectinata, Spartina spartinae*, and *Spartina×townsendii* (*S. alterniflora×S. maritima*). The parental lineage of hybrid prairie cordgrass may consist of two or more species within the Spartina genus.

Plant breeding techniques known in the art and that may be used in a prairie cordgrass plant breeding program include, without limitation, pedigree breeding, recurrent and mass selection, mutational breeding, breeding with molecular markers, production of double haploids, and male sterility and hybrid seed production. Often combinations of these techniques are used. The development of prairie cordgrass cultivars in a prairie cordgrass plant breeding program may require the development of homozygous inbred cultivars, the crossing of these cultivars, and the evaluation of the crosses. There are many analytical methods available to evaluate the result of a cross. The oldest and most traditional method of analysis is the observation of phenotypic traits, but genotypic analysis may also be used.

Accordingly, certain aspects of the present disclosure relate to methods for producing a prairie cordgrass plant by crossing a first parent prairie cordgrass plant with a second parent prairie cordgrass plant, wherein either the first or second parent is the prairie cordgrass cultivar of the present disclosure designated 'Savoy'. The other parent may be any other prairie cordgrass plant, such as another inbred cultivar or a plant that is part of a synthetic or natural population. Such crossing methods include, without limitation, pedigree breeding, selfing, backcrossing, recurrent selection, sibbing, mass selection, bulk selection, open pollination, and the like. These methods are well known in the art and some of the more commonly used breeding methods are described below. Descriptions of breeding methods can also be found in, e.g., Allard, *Principles of Plant Breeding*, 1960; Simmonds, *Principles of Crop Improvement*, 1979; and Fehr, "Breeding Methods for Cultivar Development", *Production and Uses*, 2nd ed., Wilcox editor, 1987.

Pedigree Breeding

Pedigree breeding starts with the crossing of two genotypes, such as the 'Savoy' genotype of the present disclosure, and one other cultivar, synthetic or natural population having one or more desirable characteristics that is lacking or which complements the prairie cordgrass cultivar 'Savoy'. If the two original parents do not provide all the desired characteristics, other sources can be included in the breeding population. In the pedigree method, superior plants are selfed and selected in successive filial generations. In the succeeding filial generations, the heterozygous condition gives way to homogeneous cultivars as a result of self-pollination and selection. Typically, in the pedigree method of breeding, five or more successive filial generations of selfing and selection are practiced: $F_1 \rightarrow F_2$; $F_2 \rightarrow F_3$; $F_3 \rightarrow F_4$; $F_4 \rightarrow F_5$, etc. After a sufficient amount of inbreeding, successive filial generations can serve to increase seed of the developed inbred. Preferably, the inbred cultivar comprises homozygous alleles at about 95% or more of its loci.

Backcrossing can be used in combination with pedigree breeding to modify the prairie cordgrass cultivar 'Savoy' and/or a hybrid that is made using the modified prairie cordgrass cultivar 'Savoy'. Backcrossing can be used to transfer one or more specifically desirable traits from one cultivar, the donor parent, to an inbred called the recurrent parent, which has overall good agronomic characteristics yet lacks the desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an $F_1$, such as a commercial hybrid, is created. This commercial hybrid may be backcrossed to one of its parent cultivars to create a 'backcross 1' or 'backcross 2'. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Recurrent Selection and Mass Selection

Recurrent selection may be used with the disclosed prairie cordgrass cultivar 'Savoy' to improve a population of plants. The method includes individual plants cross pollinating with each other to form progeny. The progeny are grown and the superior progeny selected by any number of selection methods, which include individual plant, half-sib progeny, full-sib progeny, selfed progeny and toperossing. The term "sibbing" refers to the act of crossing one sister plant to another "sibling" sister plant which may be a full-sib, half-sib, or variation thereof. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain inbred cultivars to be used in hybrids or used as parents for a synthetic cultivar.

Additionally, mass selection may be used with the disclosed prairie cordgrass cultivar 'Savoy'. Mass selection is a useful technique when used in conjunction with molecular marker enhanced selection. In mass selection, seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. In some instances, bulked plants are selected for their phenotype and the seeds are collected. The seeds produce plants that are phenotypically similar but may vary slightly genotypically. Plants from this selection are often called synthetic cultivars. In some instances, directed pollination, instead of self-pollination, is used as part of the breeding program. In some instances open-pollination, in which natural mechanisms such as wind, insect and animals promote pollination, is used. Any person skilled in the art would realize that pollination methods disclosed herein, without limitation, can be used in combination and in varying degrees for a prairie cordgrass breeding program.

Accordingly, certain embodiments of the present disclosure relate to a process for producing seed of the disclosed prairie cordgrass cultivar 'Savoy' by planting a collection of seed containing seed of a hybrid, one of whose parents is the prairie cordgrass cultivar 'Savoy', where the collection also contains seed of one of the parents, growing plants from the collection of seed, identifying the parent plant, selecting the parent plant; and controlling pollination to preserve the homozygosity of the parent plant.

Mutational Breeding

Mutational breeding is a method that may be used to introduce new traits into the prairie cordgrass cultivar of the present disclosure 'Savoy'. Mutations that occur spontaneously or are artificially induced can be useful sources of variability for a plant breeder. The goal of artificial mutagenesis is to increase the rate of mutation for a desired characteristic. Mutation rates can be increased by many different means including temperature; long-term seed storage; tissue culture conditions; radiation, such as X-rays, Gamma rays (e.g. cobalt 60 or cesium 137), neutrons (products of nuclear fission by uranium 235 in an atomic reactor), Beta radiation (emitted from radioisotopes such as phosphorus 32 or carbon 14), or ultraviolet radiation (preferably from 2500 to 2900 nm); or chemical mutagens, such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in Fehr, "Principles of Cultivar Development", 1993 Macmillan Publishing Company. In addition, mutations created in other cultivars may be used to produce a backcross conversion of the disclosed prairie cordgrass cultivar 'Savoy' that comprises such mutations.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing the disclosed prairie cordgrass cultivar 'Savoy'.

Isozyme Electrophoresis and RFLPs have been widely used to determine genetic composition in other monocots such as maize (Lee, M., "Inbred Lines of Maize and Their Molecular Markers," *The Maize Handbook*, Springer-Verlag, New York, Inc. 1994). The use of molecular markers in prairie cordgrass, also a monocot, is applicable as well. Well-defined molecular markers become increasingly available as more prairie cordgrass species and cultivars are sequenced. Proteome and metabolome profiles, or portions thereof, of prairie cordgrass may also be used as molecular markers in addition to nucleic acids. In addition to using Isozyme Electrophoresis and RFLPs as molecular markers, SSR technology may be used. Examples of SSR technology in maize, a monocot, have been previously described (Smith et al., *Theoretical and Applied Genetics*. Vol. 95:163-173, 1997, and Pejic et al., *Theoretical and Applied Genetics*. Vol. 97:1248-1255, 1998). SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the disclosure and progeny cultivars retaining that unique genetic composition. Various molecular marker techniques may be used in combination to enhance overall resolution.

At present, there is no linkage map available for any species of the *Spartina* genera. However, DNA molecular marker linkage maps for the moncot maize have been rapidly constructed and widely implemented in genetic studies (Boppenmaier, et al., *Maize Genetics Cooperative Newsletter*. 65:1991, pg. 90). One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. Linkage maps, which depend on well-defined molecular markers, are also applicable for use in Spartina.

Molecular markers can also be used to reduce the number of crosses back to the recurrent parent needed in a backcrossing program. With backcrossing, the expected contribution of the disclosed prairie cordgrass cultivar 'Savoy' after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. The use of molecular markers in the selection process is often called genetic marker enhanced selection. Molecular markers may also be used to confirm and/or determine the pedigree of the progeny cultivar.

Identification of self-pollinated cultivars can be accomplished through molecular marker analyses. As an example of this application, molecular markers were used to assess the purity of seed samples of two F1 hybrids in maize (Smith, J. S. C. and Wych, R. D., *Seed Science and Technology* 14, 1-8, 1995). Well-defined molecular markers become increasingly available as more prairie cordgrass species and cultivars are sequenced. Through these technologies, the homozygosity of the self-pollinated cultivar can be verified by analyzing allelic composition at various loci along the genome.

Accordingly, some embodiments of the present disclosure relate to a method of obtaining a molecular marker profile of the prairie cordgrass cultivar 'Savoy' and using the molecular marker profile to select for a progeny plant with the desired trait (e.g., the phenotype of greater biomass yield, number and size or leaves, and height) and the molecular marker profile of the prairie cordgrass cultivar 'Savoy'.

Production of Double Haploids

The production of double haploids may also be used for the development of inbreds in a breeding program. For example, an $F_1$ hybrid for which the disclosed prairie cordgrass cultivar 'Savoy' is a parent may be used to produce double haploid plants. Double haploids are produced by the doubling of a set of chromosomes (1N) from a heterozygous plant to produce a completely homozygous individual (US 2003/0005479). This can be advantageous, as the process omits the generations of selfing needed to obtain a homozygous plant from a heterozygous source.

Further examples of methods for obtaining haploid plants which may be applicable to prairie cordgrass can be found in, e.g., Kobayashi, M. et al., *Journ. of Heredity* 71(1):9-14, 1980; Pollacsek, M., *Agronomie* (Paris) 12(3):247-251, 1992; Cho-Un-Haing et al., *Journ. of Plant Biol.*, 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, *Maize Genet Coop. Newsletter* 68:47; Chalyk, S. T., 1999, *Maize Genet. Coop. Newsletter* 73:53-54; Coe, R. H., 1959, *Am. Nat.* 93:381-382; Deimling, S. et al., 1997, *Vortr. Pflanzenzuchtg* 38:203-204; Kato, A., 1999, *J. Hered.* 90:276-280; Lashermes, P. et al., 1988, *Theor. Appl. Genet.* 76:570-572 and 76:405-410; Tyrnov, V. S. et al., 1984, *Dokl. Akad. Nauk. SSSR* 276:735-738; Zabirova, E. R. et al., 1996, *Kukuruza I Sorgo* N4, 17-19; Aman, M. A., 1978, *Indian J. Genet Plant Breed* 38:452-457; Chalyk S. T., 1994, *Euphytica* 79:13-18; Chase, S. S., 1952, *Agron. J.* 44:263-267; Coe, E. H., 1959, *Am. Nat.* 93:381-382; Coe, E. H., and Sarkar, K. R., 1964 *J. Hered.* 55:231-233; Greenblatt, I. M. and Bock, M., 1967, *J. Hered.* 58:9-13; Kato, A., 1990, *Maize Genet. Coop. Newsletter* 65:109-110; Kato, A., 1997, *Sex. Plant Reprod.* 10:96-100; Nanda, D. K. and Chase, S. S., 1966, *Crop Sci.* 6:213-215; Sarkar, K. R. and Coe, E. H., 1966, *Genetics* 54:453-464; Sarkar, K. R. and Coe, E. H., 1971, *Crop Sci.* 11:543-544; Sarkar, K. R. and Sachan J. K. S., 1972, *Indian J. Agric. Sci.* 42:781-786; Kermicle J. L., 1969, Mehta Yeshwant, M. R., *Genetics and Molecular Biology*, September 2000, 23(3): 617-622; Tahir, M. S. et al. *Pakistan Journal of Scientific and Industrial Research*, August 2000, 43(4):258-261; Knox, R. E. et al. *Plant Breeding*, August 2000, 119(4):289-298; and U.S. Pat. No. 5,639,951.

Accordingly, certain embodiments of the present disclosure relate to a process for making a homozygous progeny plant from a hybrid derived from the disclosed prairie cordgrass cultivar 'Savoy' that is substantially similar to the prairie cordgrass cultivar 'Savoy' by producing or obtaining a seed from the cross of the prairie cordgrass cultivar 'Savoy' and another prairie cordgrass plant and applying double haploid methods to the $F_1$ seed or $F_1$ plant or to any successive filial generation. Such methods decrease the number of generations required to produce an inbred with similar genetics or characteristics to the prairie cordgrass cultivar 'Savoy'.

Male Sterility and Hybrid Seed Production

Other aspects of the present disclosure relate to the use of 'Savoy' to produce hybrid seed. Hybrid seed production requires elimination or inactivation of pollen produced by a female inbred parent. Incomplete removal or inactivation of the pollen provides the potential for self-pollination. A reliable method of controlling male fertility in plants offers the opportunity for improved seed production.

The prairie cordgrass cultivar 'Savoy' of the present disclosure can be produced in a male-sterile form. Many of the techniques used in maize, a monocot, may also be used in prairie cordgrass. There are several ways in which a prairie cordgrass plant may be manipulated so that it is male sterile. These include use of manual or mechanical emasculation, use of one or more genetic factors that confer male sterility, use of gametocides, and the like. The male sterility may be either partial or complete male sterility.

There are several methods of conferring genetic male sterility known in the art in monocots such as maize, including, without limitation, multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511. In addition to these methods, U.S. Pat. No. 5,432,068, describes a system of nuclear male sterility for plants in general which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed. Such methods may also be used for conferring male sterility in prairie cordgrass, such as 'Savoy'.

Other methods use a variety of approaches such as delivering into the plant a gene encoding a cytotoxic substance associated with a male tissue specific promoter or an antisense system in which a gene critical to fertility is identified and an antisense transcript to that gene is produced or inserted in the plant (see, EP 329,308 and WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied. Gametocides have been used in maize (see U.S. Pat. No. 4,936,904) and are applicable to other plant systems. Application of the gametocide, timing of the application and genotype specificity often limit the usefulness of the approach and it is not appropriate in all situations.

Male sterility is found in natural occurring prairie cordgrass populations and this trait may be bred and introduced into prairie cordgrass cultivars of interest by methods described herein and to prairie cordgrass species discussed herein (Daehler et al., *American Journal of Botany.* 1999; 86:131-139).

Various methods for transforming (introducing a transgene) a plant or plant cell are well known to those skilled in the art, and any capable of transforming the target plant or plant cell may be utilized. *Agrobacterium*-mediated transformation is perhaps the most common method utilized in plant transgenics, and protocols for *Agrobacterium*-mediated transformation of a large number of plants are extensively described in the literature (see, for example, *Agrobacterium Protocols*, Wan, ed., Humana Press, 2$^{nd}$ edition, 2006). Other commonly used transformation methods that may be employed in generating the transgenic plants of the present disclosure include, without limitation microprojectile bombardment, or biolistic transformation methods, protoplast transformation of naked DNA by calcium, polyethylene glycol (PEG) or electroporation (Paszkowski et al., 1984, EMBO J. 3: 2727-2722; Potrykus et al., 1985, Mol. Gen. Genet. 199: 169-177; Fromm et al., 1985, Proc. Nat. Acad. Sci. USA 82: 5824-5828; Shimamoto et al., 1989, Nature, 338: 274-276).

It is to be understood by those skilled in the art that methods used for maize breeding as described above, without limitation, may find utility for prairie cordgrass which, like maize, is a monocot and belongs to the same family, Poaceae. Other members of the Poaceae family include, without limitation, wheat, rice, barley, sugar cane, bamboo, rye, sorghum, millet, oats, and turf grasses. As such, those skilled in the art would realize breeding methods for the aforementioned members of the Poaceae family could have applicability to breeding in prairie cordgrass.

Tissue Culture

Other aspects of the present disclosure relate to the use of the disclosed prairie cordgrass cultivar 'Savoy' in tissue culture. As used herein, "tissue culture" includes plant protoplasts, plant cell tissue culture, cultured microspores, plant calli, plant clumps and the like. As used herein, "growing the seed" or "grown from the seed" include embryo rescue, isolation of cells from seed for use in tissue culture, as well as traditional growing methods.

In the monocot maize, methods of regenerating plants from plant tissue culture, such as callus, glume callus, and leaf segment cultures, are well known in the art (e.g., Duncan et al., *Planta* 165:322-332, 1985, Songstad et al., *Plant Cell Reports* 7:262-265, 1988, K. P. Rao, et al., *Maize Genetics Cooperation Newsletter,* 60:64-65, 1986, and B. V. Conger, et al., *Plant Cell Reports,* 6:345-347, 1987). Additionally, tissue culture of maize, including tassel/anther culture, is described in U.S. 2002/0062506A1 and European Patent Application, publication EP0160,390. Maize tissue culture procedures are also described in Green and Rhodes, *Maize for Biological Research* (Plant Molecular Biology Association, Charlottesville, Va. 1982, at 367-372); and Duncan, et al., *Planta* 165: 322-332 (1985). Tissue culture of prairie cordgrass has been described as well, and the methods of tissue culture in maize may be applicable to prairie cordgrass (Wang et al., *Wetlands* 23(2):386-393. 2003). Accordingly, other embodiments of the present disclosure provide cells which upon growth and differentiation produce prairie cordgrass plants having the genotype, physiological and/or morphological characteristics of the disclosed prairie cordgrass cultivar 'Savoy'.

It will be understood that in addition to the methods of chemical mutagenesis, selection, generating tissue culture from plant material, crossing, and growing plants described herein, any other methods of chemical mutagenesis, selection, generating tissue culture from plant material, crossing and growing plants known in the art may be used.

Uses of Prairie Cordgrass

Prairie cordgrass 'Savoy' of the present disclosure may have many uses including, without limitation, production of biomass for use as a bioenergy feedstock, for erosion control, and for bioconservation and remediation.

Bioenergy Feedstock

Prairie cordgrass 'Savoy' of the present disclosure can be used to produce a bioenergy feedstock. This bioenergy feedstock may be used in the production of a biofuel such as ethanol or butanol. Methods of producing bioenergy feedstocks from biomass are well known in the art.

The methods described herein can be practiced in combination with other methods useful for converting prairie cordgrass biomass into bioenergy feedstock. Bioenergy feedstocks may include, without limitation, cellulose, hemicellulose, lignin, and carbohydrates. Such feedstocks can be used for the production of hydrocarbons, and hydrocarbon derivatives, such as biofuels. Pretreatment, such as by chemical, physical or enzymatic means, of the bioenergy feedstock may be required prior to feedstock processing in order for the feedstock to be adequate for production of hydrocarbons and hydrocarbon derivatives.

Biomass Source

Prairie cordgrass cultivars of the present disclosure, such as 'Savoy', may be used as a source of biomass containing cellulose and hemicellulose as some of their most abundant biomass components. Cellulose is an unbranched polysaccharide composed on long chains of β(1-4) linked D-glucose molecules. Hemicellulose, a branched shorter polysaccharide is also composed of sugar monomers, but is not exclusively composed of D-glucose, and may contain xylose, mannose, galactose, rhamnose, and arabinose or combinations thereof. Due to their sugar-based composition, cellulose and hemicellulose are a rich potential source material for the production of biofuels. For example, the sugars present in these polymers may be fermented into biofuels such as ethanol. In order for the sugars within cellulose and hemicellulose to be used for the production of biofuels, the cellulose and hemicellulose must be broken down into smaller molecules by pretreatment and processing of the biomass. Once the biomass broken down, it may be used for the production of bioenergy feedstocks and biofuels.

In some embodiments, the biomass is cellulosic or lignocellulosic biomass. Cellulosic biomass includes cellulose and/or hemicellulose, whereas lignocellulosic biomass further includes lignin. Lignin is a structural component of the plant secondary cell wall and provides rigidity to plants.

Additionally, in certain embodiments biomass from prairie cordgrass cultivars of the present disclosure, such as 'Savoy', may be combined with additional biomass sources for the production of a bioenergy feedstock. Examples of additional biomass sources include, without limitation, grass, switch grass, rye grass, reed canary grass, miscanthus, mixed prairie grasses, sugar-processing residues, sugarcane bagasse, agricultural wastes, rice straw, rice hulls, barley straw, corn cobs, cereal straw, wheat straw, canola straw, oat straw, oat hulls, beet pulp, palm residue, corn fiber, stover, soybean stover, corn stover, corn cob, herbaceous materials, agricultural residues, municipal solid waste, forestry wastes, recycled wood pulp fiber, paper sludge, waste paper, pulp and paper mill residues, sawdust, hardwood, softwood and combinations thereof.

Pretreatment of Bioenergy Feedstock

In some embodiments, the prairie cordgrass biomass may be pretreated to make any cellulose and hemicellulose components more accessible and susceptible to hydrolysis. Methods for pretreating biomass are well known in the art and include, without limitation, chemical pretreatment, physical pretreatment, biological pretreatment methods and combinations thereof.

In some embodiments, pretreatment of prairie cordgrass biomass may include chemical pretreatment, such as chemical hydrolysis, to remove lignin from the biomass material to increase the overall amount of released sugar. Any method known in the art for chemical hydrolysis may be employed, including, without limitation, contacting the biomass with a chemical (e.g., an acid or an alkali) for a period of time at a specific temperature that yields at least some disaccharides and/or monosaccharides from the polymeric cellulose and hemicellulose in the biomass.

In other embodiments, prairie cordgrass biomass is subjected to physical pretreatment. Such physical pretreatment may include, without limitation, heat, mechanical agitation, irradiation (e.g., microwave irradiation), steaming/steam explosion, or hydrothermolysis. A combination of physical pretreatment methods may also be employed. For example, a combination of thermochemical pretreatment involving acid hydrolysis, heat and mechanical agitation may be used to break down cellulose and hemicellulose into simple sugars.

In other embodiments pretreatment of prairie cordgrass biomass includes biological treatment, such as enzymatic hydrolysis. Any method known in the art for enzymatic hydrolysis may be employed, including, without limitation, contacting the biomass with a saccharification enzyme or an organism capable of expressing or secreting a saccharification enzyme. Examples of saccharification enzymes include, without limitation, cellulases, hemicellulases, endoglucanases, exoglucanases, cellobiohydrolases, β-glucosidases, xylanases, endoxylanases, exoxylanases, β-xylosidases, arabinoxylanases, mannases, galactases, pectinases, glucuronidases, amylases, glucoamylases, α-glucosidases and isoamylases. See e.g., U.S. 2010/0285534 for examples of enzymes. Organisms capable of expressing or secreting a saccharification enzyme may include bacteria or yeast.

Hydrocarbons and Carbohydrates

In certain embodiments, prairie cordgrass plants of the present disclosure and biomass harvested therefrom can be processed to produce hydrocarbons and hydrocarbon derivatives. Such processing may include, without limitation, wet or dry milling, fermentation, chemical processing, distillation, and combinations thereof. As disclosed herein, hydrocarbons or hydrocarbon derivatives find numerous uses including, without limitation, use as fuels.

Prairie cordgrass cultivars of the present disclosure, such as 'Savoy', can be utilized for the production of hydrocarbons and hydrocarbon derivatives, such as biofuels. Methods for producing hydrocarbons and hydrocarbon derivatives from bioenergy feedstocks are well known in the art and include, without limitation, those disclosed herein. "Hydrocarbons" as used herein are organic compounds consisting entirely of hydrogen and carbon. Hydrocarbons include, without limitation, methane, ethane, ethane, ethyne, propane, propene, propyne, cyclopropane, allene, butane, isobutene, butane, butyne, cyclobutane, methylcyclopropane, butadiene, pentane, isopentane, neopentane, pentene, pentyne, cyclopentane, methylcyclobutane, ethylcyclopropane, pentadiene, isoprene, hexane, hexane, hexyne, cyclohexane, methylcyclopentane, ethylcyclobutane, propylcyclopropane, hexadiene, heptane, heptene, heptyne, cycloheptane, methylcyclohexane, heptadiene, octane, octane, octyne, cyclooctane, octadiene, nonane, nonene, nonyne, cyclononane, nonadiene, decane, decene, decyne, cyclodecane and decadiene.

"Hydrocarbon derivatives" as used herein are organic compounds of carbon and at least one other element that is not hydrogen. Hydrocarbon derivatives include, without limitation, alcohols (e.g., butanol, ethanol); organic acids; esters; ketones; aldehydes; amino acids; and gases. In certain preferred embodiments, prairie cordgrass cultivars of the present disclosure, such as 'Savoy', are used in the production of ethanol and/or butanol.

Prairie cordgrass plants of the present disclosure can also be utilized for the production of carbohydrates (i.e., saccharides). Carbohydrates include compounds containing carbon, oxygen and hydrogen and as discussed herein may include monomers and polymers of these compounds. Carbohydrates include, without limitation, polysaccharides, oligosaccharides, monosaccharides, glucose, glucan, dextrose, sucrose and fructose. The 'Savoy' prairie cordgrass plants can be subjected to wet or dry milling, saccharification and processing to produce carbohydrates. Carbohydrates find numerous uses including use as food sweeteners and use in the production of fuels.

Further, it should be understood that the biomass used to provide the bioenergy feedstock may be subjected to a one-step or a multi-step treatment process. For example, in some embodiments, the biomass is first contacted with an acid, and then the resulting product is contacted with one or more enzymes in a second hydrolysis to yield fermentable sugars and the biomass composition. Any person skilled in the art will recognize methods, and combinations of methods, for processing biomass into a feedstock, and subsequent production of hydrocarbon, hydrocarbon derivatives and carbohydrates.

Biofuels from Bioenergy Feedstocks

Other aspects of the present disclosure relate to the use of bioenergy feedstocks derived from prairie cordgrass cultivars of the present disclosure, such as 'Savoy', in the production of biofuels, such as ethanol.

For example, ethanol can be produced by enzymatic conversion (e.g., fermentation) of bioenergy feedstocks, such as carbohydrates. This kind of ethanol is often referred to as bioethanol or biofuel. It can be used as a fuel additive or extender in blends of from less than 1% and up to 100% (a fuel substitute). Biofuels may be produced from bioenergy feedstocks, such as carbohydrates, produced by the methods disclosed herein by any technique known in the art including, without limitation, microbial or chemical fermentation and biological synthesis.

Microorganisms that are suitable for microbial fermentation are able to convert carbohydrates; sugars, such as glucose, xylose, arabinose, mannose, galactose; or oligosaccharides, directly or indirectly into the desired biofuel or bioproduct. Examples of suitable fermentation microorganisms include, without limitation, yeast, fungi, algae, bacteria and combinations thereof.

Erosion Control

In certain embodiments, prairie cordgrass cultivars of the present disclosure, such as 'Savoy', may be used for erosion control and bioconservation. Such a use may include, without limitation, planting seedlings, cuttings, rhizomes and/or seeds of prairie cordgrass cultivars of the present disclosure, sure as 'Savoy'.

Erosion control may include, without limitation, assessing erosion potential by identifying areas of land that are subject to run-on and runoff, assessing the impact of planting additional vegetation, and planting additional vegetation. Examples of suitable types of vegetation that may be planted includes, without limitation, prairie cordgrass cultivars of the present disclosure, such as 'Savoy'. As rhizmatous, sod-forming perennial grasses, prairie cordgrass cultivars, such as 'Savoy', are well suited to control soil erosion by virtue of their root mass that helps hold the soil together and prevents wind and water from easily eroding the surrounding soil. In turn, reduced soil erosion positively contributes to the stabilization of highly erodible landscapes, such as stream banks.

Accordingly, in certain embodiments, prairie cordgrass cultivars of the present disclosure, such as 'Savoy', can be utilized to stabilize a stream bank by planting the prairie cordgrass on the stream banks to control soil erosion, thereby stabilizing the stream bank.

Bioconservation and Remediation

In other embodiments, prairie cordgrass cultivars of the present disclosure, such as 'Savoy', may be used in bioconservation and remediation applications, such as revegetation.

Remediation through revegetation may include, without limitation, identifying areas in need of revegetation, preparation of the soil area through various means such as application of fertilizer and mulch to the soil, planting prairie cordgrass cultivars of the present disclosure, such as 'Savoy', and maintaining the remediated area through irrigation and fertilizing until the new vegetation is well established. Revegetated areas benefit from soil conservation efforts such as perimeter runoff control and salinity management. For example, due to their salt tolerance, prairie cordgrass cultivars of the present disclosure, such as 'Savoy', may be planted in high saline soil and used remove salts from soil by harvesting the foliage, which contains a portion of the salts. Revegetated areas may further benefit bioconservation efforts by providing additional resources and habitats for foraging and shelter that can promote ecosystem biodiversity.

Accordingly, in certain embodiments, prairie cordgrass cultivars of the present disclosure, such as 'Savoy', can be utilized for remediating salt-affected soil by growing the prairie cordgrass in salt-affected soil under conditions sufficient for the prairie cordgrass to absorb salt from the salt-affected soil; and harvesting the prairie cordgrass, thereby removing the salt from the soil.

Additionally, the seed of prairie cordgrass cultivars of the present disclosure, such as 'Savoy', the plant produced from such seed, the hybrid prairie cordgrass plant produced from the crossing of such a cultivar, hybrid seed, and various parts of the hybrid prairie cordgrass plant may be utilized for any of the disclosed uses.

It is to be understood that, while the seeds, plants, and methods disclosed herein have been described in conjunction with the preferred embodiments thereof, the foregoing description is intended to illustrate and not limit the scope thereof as defined in the appended claims. Other aspects, advantages and modifications within the scope thereof as defined in the appended claims will be apparent to those skilled in the art to which the present disclosure pertains.

EXAMPLES

The following Example is merely illustrative and is not meant to limit any aspects of the present disclosure in any way.

Example 1

Growth Characteristics and Morphology

The following example describes a comparative study of the commercially available prairie cordgrass cultivar 'Red River' to the novel cultivar 'Savoy'.

TABLE 1

| Traits | 'Red River' | 'Savoy' |
|---|---|---|
| Ploidy | Octaploid | Tetraploid |
| Rhizome type | Phalanx | Guerilla |
| Biomass yield (Mg/ha): | 10 | 24 |
| Tillers $m^{-2}$ | 308 | 130 |
| Mass tiller$^{-1}$ (g) | 3.1 | 19.9 |
| Leaves tiller$^{-1}$ (no.) | 6.5 | 9.2 |
| Shoot height (m) | 1.2 | 2.1 |
| Leaf blade length (cm): | | |
| 1st leaf | 38 | 103 |
| 5th leaf | 87 | 106 |
| Leaf blade width (mm): | | |
| 1st leaf | 5 | 15 |
| 5th leaf | 13 | 17 |
| Leaf weight (g): | | |
| 1st leaf | 0.1 | 1.0 |
| 5th leaf | 0.8 | 1.2 |

In Table 1, data for above-ground biomass yield and morphological characteristics of 'Savoy' and 'Red River' prairie cordgrass (*Spartina pectinata*) was collected during the growing season of year 3 and year 4 at Urbana, Ill.

In growing season of year 3 and year 4, the biomass yield of cultivar 'Savoy' was 2.4 fold greater than that of cultivar 'Red River'. While the overall number of tillers was reduced from 380 to 130 per $m^2$, the mass per individual tiller increased from 3.1 to 19.9 grams in cultivar 'Savoy' and 'Red River', respectively. The number of leaves per tiller also increased, and the shoot height nearly doubled, respectively. Leaf blade length, width and weight also increased for 'Savoy' relative to 'Red River'. The ploidy level of 'Savoy' is tetraploid, while that of 'Red River' is octaploid. The type of rhizome also differs between 'Savoy' and 'Red River' and is guerilla-type and phalanx-type, respectively (Table 1).

DEPOSIT INFORMATION

A deposit of the prairie cordgrass cultivar 'Savoy' is maintained by EBI Energy Farm, having an address at 4110 S Race St, Urbana, Ill. 61801, United States. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the cultivar will be irrevocably removed by affording access to a deposit of at least 2,500 seeds of the same cultivar with the American Type Culture Collection, (ATCC), P.O. Box 1549, MANASSAS, Va. 20108 USA.

At least 2500 seeds of prairie cordgrass 'Savoy' were deposited on Nov. 4, 2013 according to the Budapest Treaty in the American Type Culture Collection (ATCC), ATCC Patent Depository, 10801 University Boulevard, Manassas, Va., 20110, USA. The deposit has been assigned ATCC number PTA-120691. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the cultivar will be irrevocably removed for the enforceable life of the patent.

The deposit will be maintained in the ATCC depository, which is a public depository, for a period of 30 years, or 5 years after the most recent request, or for the effective life of the patent, whichever is longer, and will be replaced if a deposit becomes nonviable during that period.

The invention claimed is:

1. Seed of prairie cordgrass cultivar designated 'Savoy', representative seed of said cultivar having been deposited under ATCC Accession Number PTA-120691.

2. A prairie cordgrass plant produced by growing the seed of claim 1.

3. Pollen of the plant of claim 2.

4. An ovule of the plant of claim 2.

5. Tissue culture of the plant of claim 2.

6. A plant part from the plant of claim 2.

7. The plant part of claim 6, wherein said plant part is a leaf, a blade, a stalk, a shoot, a rhizome, a tiller, or a portion thereof.

8. A prairie cordgrass plant having all the physiological and morphological characteristics of the prairie cordgrass plant of claim 2.

9. A method of producing prairie cordgrass seed, comprising:
   a) crossing prairie cordgrass cultivar designated 'Savoy' with itself or another prairie cordgrass, wherein representative seed of said cultivar 'Savoy' having been deposited under ATCC Accession Number PTA-120691; and
   b) harvesting seed therefrom.

10. A method of producing a hybrid prairie cordgrass seed, comprising:
   a) crossing a first prairie cordgrass plant with a second prairie cordgrass plant, wherein said first or second prairie cordgrass plant is the prairie cordgrass plant of claim 2; and
   b) harvesting seed therefrom.

11. A method of selecting prairie cordgrass, comprising:
   a) growing more than one plant from the seed of claim 1; and
   b) selecting one or more plants from step a).

12. A bioenergy feedstock produced from the plant of claim 2 or a part thereof.

13. A method of producing a bioenergy feedstock, comprising:
   a) obtaining biomass derived from the plant of claim 2; and
   b) processing said biomass to produce a bioenergy feedstock.

14. The method of claim 13, wherein processing said biomass comprises pretreating said biomass.

15. The method of claim 14, wherein the pretreating comprises chemical pretreatment of said biomass, physical pretreatment of said biomass, biological pretreatment of said biomass, or a combination thereof.

16. The method of claim 13, further comprising producing a biofuel from said bioenergy feedstock.

17. A method of controlling soil erosion, comprising growing plants from the seed of claim 1 under conditions suitable for the resulting plants to control soil erosion.

18. A method of stabilizing a stream bank, comprising growing plants from the seed of claim 1 under conditions suitable for the resulting plants to control soil erosion along the stream bank, thereby stabilizing said stream bank.

19. A method for remediating salt-affected soil, comprising:
   a) growing plants from the seed of claim 1 under conditions sufficient for the resulting plants to absorb salt from the salt-affected soil; and
   b) harvesting said plants, thereby removing said salt from the soil.

* * * * *